United States Patent
Abbud-Antaki (10) Patent No.: US 7,537,913 B2
(45) Date of Patent: May 26, 2009

(54) HIGH THROUGHPUT ASSAY FOR CANCER CELL GROWTH INHIBITION

(75) Inventor: Rula Abbud-Antaki, Allison Park, PA (US)

(73) Assignee: Falcon Genomics, Inc., Pittsburgh, PA (US)

( * ) Notice: Subject to any disclaimer, the term of this patent is extended or adjusted under 35 U.S.C. 154(b) by 27 days.

(21) Appl. No.: 11/337,215

(22) Filed: Jan. 20, 2006

(65) Prior Publication Data
US 2006/0166247 A1 Jul. 27, 2006

Related U.S. Application Data

(60) Provisional application No. 60/646,210, filed on Jan. 21, 2005.

(51) Int. Cl.
C12Q 1/18 (2006.01)
C12M 1/34 (2006.01)

(52) U.S. Cl. .................. 435/32; 435/33; 435/287.9; 435/288.4; 435/288.7; 359/396; 359/398

(58) Field of Classification Search .............. 435/32, 435/33, 287.9, 288.4; 359/396, 398
See application file for complete search history.

(56) References Cited

U.S. PATENT DOCUMENTS

| | | | | |
|---|---|---|---|---|
| 4,011,350 A | * | 3/1977 | Markovits et al. | 427/2.13 |
| 4,790,640 A | * | 12/1988 | Nason | 359/396 |
| 6,706,520 B2 | * | 3/2004 | Han et al. | 435/287.9 |
| 2002/0006664 A1 | * | 1/2002 | Sabatini | 435/456 |
| 2003/0044389 A1 | * | 3/2003 | Brown et al. | 424/93.7 |
| 2004/0248164 A1 | * | 12/2004 | Chi et al. | 435/6 |

OTHER PUBLICATIONS

Ziauddin et al., Microarrays of cells expressing defined cDNAs, 2001, Nature 411(6833): 107-110.
Mousses et al., RNAi Microarray Analysis in Cultured Mammalian Cells, 2003, Genome Res. 13(10): 2341-2347.
Kumar et al., High-Throughput Selection of Effective RNAi Probes for Gene Silencing, 2003, Genome Res. 13(10):2333-2340.
Silva et al., RNA interference microarrays: high-throughput loss-of-function genetics in mammalian cells, 2004, Proc. Natl. Acad. Sci. 101(17): 6548-6552.
Baghdoyan et al., Quantitative analysis of highly parallel transfection in cell microarrays, 2004, Nucleic Acids Res. 32(9):e77.
Paddison et al., Short Hairpin Activated Gene Silencing in Mammalian Cells, 2004, Methods Mol. Biol. 265:85-100.
Berns et al., A large-scale RNAi screen in human cells identifies new components of the p53 pathway, 2004, Nature 428(6981):431-437.

(Continued)

Primary Examiner—William H Beisner
(74) Attorney, Agent, or Firm—Eckert Seamans Cherin & Mellott, LLC; Peter D. Mlynek (57) ABSTRACT

A high-throughput, anchorage-independent assay is described, which screens compounds for inhibition of cancer cell growth. The assay utilizes a three-dimensional matrix or semi-solid media transfected with the subject compound, and enables live colony growth determination and imaging.

38 Claims, 5 Drawing Sheets
(2 of 5 Drawing Sheet(s) Filed in Color)

OTHER PUBLICATIONS

Shoemaker et al., Experimental annotation of the human genome using microarray technology, 2001, Nature 409(6822):922-927.

Venter et al., The sequence of the human genome, 2001, Science 291(5507):1304-1351.

Van't Veer et al., Gene expression profiling predicts clinical outcome of breast cancer, 2002, Nature, 415(6871):530-536.

Pavey et al., Microarray expression profiling in melanoma reveals a BRAF mutation signature, Oncogene 23(23):4060-4067.

Van De Vijver et al., A Gene-Expression Signature as a Predictor of Survival in Breast Cancer, 2002, N. Eng. J. Med. 347(25):1999-2009.

Matzke et al., Homology-dependent gene silencing in transgenic plants: epistatic silencing loci contain multiple copies of methylated transgenes, 1994, Mol. Gen. Genet. 244(3):219-229.

Jorgensen et al., Chalcone synthase cosuppression phenotypes in petunia flowers: comparison of sense vs. antisense contructs and single-copy vs. complex T-DNA sequences, 1996, Plant Mol. Biol. 31(5):957-973.

Elbashir et al., Analysis of gene function in somatic mammalian cells using small interfering RNAs, 2002, Methods 26(2):199-213.

Caplen et al., Specific inhibition of gene expression by small double-stranded RNAs in invertebrate and vertebrate systems, 2001, Proc. Natl. Acad. Sci. 98(17):9742-9747.

Caplen et al., Short Interference RNA (siRNA)-Mediated RNA Interference (RNAi) in Human Cells, 2003, App. N.Y. Acad. Sc. 1002:56-62.

McManus et al., Gene Silencing in Mammals by Small Interfering RNAs, 2002, Natl. Rev. Genet. 3(10):737-747.

Calegari et al., Tissue-specific RNA interference in postimplatation mouse embryos with endoribonuclease-prepared short interfering RNA, 2002, Proc. Natl. Acad. Sci. 99(22):14236-14240.

Yang et al., Short RNA duplexes produced by hydrolysis with *Escherichia coli* RNase III mediate effective RNA interference in mammalian cells, 2002, Proc. Natl. Acad. Sci 99(15):9942-9947.

Henschel et al., DEQOR: a web-based tool for the design and quality control of siRNAs, 2004, Nucleic Acids Res. 32(Web server issue): W113-W120.

Naito et al., siDirect: highly effective, target-specific siRNA design software for mammalian RNA interference, 2004, Nucleic Acids Res. 32(Web server issue):W124-W129.

Dudek et al., TROD:T7 RNAi Oligo Designer, 2004, Nucleic Acids Res. 32 (Web server issue):W121-W123.

Paddison et al., A resource for large-scale RNA-interference-based screens in mammals, 2004, Nature, 428(6981):427-431.

Gupta et al., Inducible, reversible, and stable RNA interference in mammalian cells, 2004, Proc. Natl. Acad. Sci, 101(7):1927-1932.

Hannon et al., RNA Interference by Short Hairpin RNAs Expressed in Vertebrate Cells, 2004, Methods Mol. Biol. 257:255-266.

Jacks et al., Taking the Study of Cancer Cell Survival to a New Dimension, 2002, Cell 111(7):923-925.

Kleinman et al., Basement Membrane Complexes with Biological Activity, 1986, Biochemistry 25(2):312-318.

Karp et al., Bone formation on two-dimensional poly (DL-lactide-co-glycolide) (PLGA) films and three-dimensional poly PLGA tissue engineering scaffolds in vitro, 2003, J. Biomed. Mater. Res. 64A(2):388-396.

Chevallay et al., Collagen-based biomaterials as 3D scaffold of cell cultures: applications for tissue engineering and gene therapy, 2000, Med. Biol. Eng. Comput. 38(2):211-218.

Thornton et al., Shape-Defining Scaffolds for Minimally Invasive Tissue Engineering, 2004, Transplantation 77(12);1798-1803.

Kupchik et al., A New Method for the Three-Dimensional in vitro Growth of Human Cancer Cells, 1983, Exp. Cell Res. 147(2):454-460.

Zhang, Emerging biological materials through molecular self-assembly, 2002, Biotechnol. Adv. 20(5-6):321-339.

Kisiday et al., Self-assembling peptide hydrogel fosters chondrocyte extracellular matrix production and cell division: implications for cartilage tissue repair, 2002, Proc. Natl. Acad. Sci. USA 99(15):9996-10001.

Holmes et al., Extensive neurite outgrowth and active synapse formation on self-assembling peptide scaffolds, 2000, Proc. Natl. Acad. Sci. USA 97(12):6728-6733.

Abbud et al., Chronic Hypersecretion of Luteinizing Hormone in Transgenic Mice Selectively Alters Responsiveness of the α-Subunit Gene to Gonadotropin-Releasing Hormone and Estrogens, 1999, Mol. Endocrinol. 13(9):1449-1459.

Flaws et al., Chronically Elevated Luteinizing Hormone Depletes Primordial Follicles in the Mouse Ovary, 1997, Biol. Reprod. 57(5):1233-1237.

Mohammad et al., Targeted Overexpression of Luteinizing Hormone Causes Ovary-Dependent Functional Adenomas Restricted to Cells of the Pit-1 Lineage, 2003, Endocrinology 144(10):4626-4636.

Nilson et al., Chronic Hypersecretion of Luteinizing Hormone in Transgenic Mice Disrupts Both Ovarian and Pituitary Function, with Some Effects Modified by the Genetic Background, 2000, Recent Prog. Horm. Res. 55:69-89.

Abbud et al., Cell-Specific Pituitary Gene Expression Profiles after Treatment with Leukemia Inhibitory Factor Reveal Novel Modulators for Proopiomelanocortin Expression, 2004, Endocrinology 145(2):867-880.

Farmerie et al., Characterization of the Equine Glycoprotein Hormone Alpha-Subunit Gene Reveals Divergence in the Mechanism of Pituitary and Placental Expression, 1997, Biol. Reprod. 57(5):1104-1114.

Ikeda et al., The Nuclear Receptor Steroidogenic Factor 1 is Essential for the Formation of the Ventromedial Hypothalamic Nucleus, 1995, Mol. Endocrinol. 9(4):478-486.

Ingraham et al., The nuclear receptor steroidogenic factor 1 acts at multiple levels of the reproductive axis, 1994, Genes Dev. 8(19):2302-2312.

Lee et al., LHRH Neurons Express cJun Protein during the Proestrous Surge of Luteinizing Hormone, 1992, Endocrinology 130(5):3101-3103.

Lee et al., Effects of N-Methyl-D-Aspartate Receptor Activation on cFos Expression in Lluteinizing Hormone-Releasing Hormone Neurons in Female Rats, 1993, Endocrinology 130(5):2248-2254.

Hoffman et al., c-Fos and Fos-Related Antigens as Markers for Neuronal Activity: Perspectives from Neuroendocrine Systems, 1993, NIDA Res. Monogr. 125:117-133.

Hoffman et al., Use of Fos-related antigens (FRAs) as markers of neuronal activity: FRA changes in dopamine neurons during proestrus, pregnancy and lactation, 1994, Brain Res. 654(2):207-215.

Abbud et al., Lactation-induced deficits in NMDA receptor-mediated cortical and hippocampal activation changes in NMDA receptor gene expression and brainstem activation, 1994, Brain Res. Mol. Brain Res. 25(3-4):323-332.

Abbud et al., Cortical refractoriness to N-methyl-D, L-aspartic acid (NMA) stimulation in the lactating rat: recovery after pup removal and blockade of progesterone receptors, 1993, Brain Res. 604(1-2):16-23.

Abbud et al., Do GnRH neurons express the gene for the NMDA receptor? 1995, Brain Res. 690(1):117-120.

Nadeau, Modifying the Message, 2003, Science 301(5635):927-928.

Nadeau, Modifier genes and protective alleles in humans and mice, 2003, Curr. Opin. Genet. Dev. 13(3):290-295.

Nadeau, Single nucleotide polymorphisms: tackling complexity, 2002, Nature 420(6915):517-518.

Singer et al., Genetic Dissection of Complex Traits with Chromosome Substitution Strains of Mice, 2004, Science 304(5669):445-448.

Roy et al., Microscope-based techniques to study cell adhesion and migration, 2002, Nat. Cell Biol. 4(4):E91-E96.

Roy et al., Effect of Cell Migration on the Maintenance of Tension on a Collagen Matrix, 1999, Ann. Biomed. End. 27(6):721-730.

Silva et al., RNA interference: a promising approach to antiviral therapy? 2002, Trends Mol. Med. 8(11):505-508.

Murayama et al., Regulation of Human Estrogen Receptor Gene, Epidermal Growth Factor Receptor Gene and Oncogenes by Estrogen and Antiestrogen in MCF-7 Breast Cancer Cells, 1988, Cancer Det. Prev. 13(2):103-107.

Eshre Capri Workshop Group, Hormones and breast cancer, 2004, Human Reprod. Update, 10(4):281-293.

Jordan, Selective Estrogen Receptor Modulation: A Personal Perspective, 2001, Cancer Res. 61(15):5683-5687.

Schiffer et al., Switching off HER-2/neu in a Tetracycline-Controlled Mouse Tumor Model Leads to Apoptosis and Tumor-Size-Dependent Remission, 2003, Cancer Res. 63(21):7221-7231.

* cited by examiner

HIGH THROUGHPUT ASSAY FOR CANCER CELL GROWTH INHIBITION

CROSS REFERENCES AND RELATED APPLICATIONS

The application claims priority from U.S. Provisional Application Ser. No. 60/646,210 entitled "HIGH THROUGHPUT ASSAY FOR CANCER DRUG DISCOVERY", filed on Jan. 21, 2005, herein incorporated by reference in its entirety.

BACKGROUND

Current treatments for many types of cancer are primitive. Chemotherapies and radiation treatments kill diseased and healthy cells indiscriminately resulting in great discomfort to the patient and many side-effects. Understanding the molecular events involved in tumorigenesis will enable the development of cancer therapies that target specific genes and proteins within diseased cells producing therapies that are more effective and less toxic to the patient. The development of a method for rapidly screening potential therapies and molecular targets would greatly enhance the ability of researchers to develop new targeted cancer treatments that are less toxic to healthy cells.

The entire sequence of the human genome is now published, however the function of many genes remain unassigned. Recent advances in DNA microarray technology have allowed for the identification of genes expressed in many human cell types and provided a method of detecting abnormal gene expression in cancer cells. Hundreds of genes whose expression is altered in cancer cells have been identified in this way. Current functional genomic technologies are limited since only one gene can be analyzed at a time, and these techniques are unable to determine the extent to which each gene contributes to abnormal growth in cancer cells when multiple genes are involved.

Diseased cells may contain a mutated or mis-expressed gene that effects several protein signaling pathways that each contribute to the cancerous phenotype. A particularly effective cancer treatment would either specifically target the affected gene or target genes in each of the affected pathways. In either case, it is necessary to understand the expression patterns of a great number of potential targets and to have methods for modulating expression of each potential target. Thus, a high-throughput method for functional genomic screening and inhibitor design is required for the identification of cancer therapeutic agents.

Anchorage-independent growth is the gold-standard for in vitro testing of potential chemotherapeutic agents. Tumorigenic cells do not exhibit contact inhibition and can grow independently of extracellular matrix (ECM) binding. Normal cells cannot. Therefore, only tumorigenic cells grow in three dimensions on soft agar devoid of ECM. Currently, anchorage-independent growth assays can only test one inhibitor at a time or several inhibitors in 96 well plates. A separate transfection step is required in either case, and these methods require a large amount of biopsy tissue to obtain sufficient colony growth and cells need to be stained for quantification. A high-throughput assay for anchorage-independent growth that does not require killing the cells prior to imaging is desirable. In addition, one-step transfection is desirable.

The limitations described above and the ability of tumorigenic cells to grow in the absence of ECM make it desirable to develop a reverse transfection microarray system in which cells are grown in a matrix devoid of ECM. This system will use less biopsy tissue and allow for tumorigenic cell specific growth while more closely mimicking the in vivo environment of cancer cells.

SUMMARY

The present invention is directed to a device for assaying cells that is made up of a slide that is coated with a matrix that supports anchorage-independent, three-dimensional cell growth. Spots containing active agents are placed in or on the matrix, and cells are plated on the matrix and allowed to grow in the presence of the active agents.

The slide may be any type of slide including: glass slides, plastic slides, polystyrene slides, quartz wafers or combinations of types slide. Spots may be physically separated from one another and deter cell migration between spots on the slide by wells made up of orifices within the slide or may have a removable member with orifices with in the member applied to one side of the orifices define wells that provide the physical barrier. Alternatively, etched demarcations in the slide may separate the spots and provide the physical barrier between spots.

The matrix is, generally, from about 0.1 mm to about 1 mm thick and provides an environment in which cancer cells can grow into discrete colonies. Any of the following coatings or a combination coatings may be used in the present invention: soft agar, agarose, hydrogels, methylcellulose alginate hydrogel, polyvinyl alcohol-hydrogel, collagen vitrigel, poly(2-hydroxylmethacrylate) hydrogels, PVP/PEO hydrogels or copolymers of 2-methacryloyloxyethyl phophorylcholine and. The matrix allows for the cells plated on the slide form discrete colonies.

In a preferred embodiment of the invention, the matrix is soft agar.

The matrix may hold a great number of active agents or combinations of active agents including: DNA, RNA, siRNA, shRNA, antibodies, small molecules, proteins, peptides, peptidomimetics, pharmaceutical compositions and drugs. Each slide is able to hold from about 1 to about 150,000 spots that are about 65 to about 120 μm in diameter. The active agents spotted on the matrix coated slide, generally, target a gene or a gene product, preferably a gene.

In a preferred embodiment of the invention, an active agent targeting each gene in the human genome is spotted on the slide or set of slides with each active agent having a discrete location. An active agent for each expressed human gene may also be spotted on the slide.

In a preferred embodiment of the invention, the spots are siRNA.

The matrix may also include a transfection which can be any or any combination of the following: chemical transfection agents, lipid based transfection agents, cationic lipid transfection agents, non-lipid based transfection agents, electroporation, molecular-based transfections, laser mediated transfection, pinocytosis transfection, ostmotic lysis transfection, microinjection and viral delivery systems.

The cells that are plated on the slide are, generally, cancerous cells but may include any or any combination of the following cell types: cultured cells, cancer cells, tissue sample cells, tumor cells, tumor cells derived from the biopsy of a cancer patient, normal cells derived from a healthy patient, known cell lines, and combinations thereof.

The cells plated on the matrix coated slide may also contain a detectable label that can be any or any combination of the following labels and markers: selectable markers, fluorescent markers, fluorescent nanocrystals, quantum dots, fluorescent proteins, bacterial enzymes. Live unlabeled cells may also be plated on the slide of the present invention.

The cells plated on the matrix coated slide can be observed by a number of methods or combinations of methods including: microscopy, scanning, laser scanning, fluorescence detection, automated fluorescence detection, a CCD camera, cell counter, automated colony counter, the human eye, FACS.

The device may also include slide that is a calibration chip that has control agents spotted on or in the matrix.

The present invention also includes a method of using the slides as described above to isolate cancer inhibiting active agent that includes: coating a slide with a matrix capable of supporting anchorage-independent three-dimensional cell growth, spotting active agents onto or into the matrix at distinct locations on the slide, adding cells to the slide, measuring cell growth on each spot, identifying the active agent that corresponds to the spot, and identifying the active agent that corresponds to the spot. Cell growth can be observed using the methods for observing cells above and measured using a computer program. Spots on which cell growth is inhibited indicate that the active agent or combination of active agents on that spot are cancer inhibiting active agents.

A method for identifying a cancer causing gene using the slide as described above is also encompassed in the present invention. This method includes: coating slide with a matrix capable of supporting anchorage-independent, three-dimensional cell growth, spotting active agents on or into the matrix at separate distinct locations on the slide wherein each active agent is capable of inhibiting expression of a single, specific target gene, plating cancerous cells onto the slide wherein the cancerous cells take up of the active agent when plated, detecting colonies of living cancerous cells, determining the spots on which cancerous cell growth is inhibited, identifying the active agent that corresponds with the spot on which cancerous cell growth is inhibited, relating the specific active agent with the gene whose expression the active agent inhibits and determining the gene whose expression inhibition inhibits growth of cancerous cells.

In a preferred embodiment of this method, the chip contains an active agent inhibitor for every human gene or every expressed human gene spotted at a discrete location.

In a particularly preferred embodiment of the method, live cells are observed in real time, and their growth is measured over time.

DESCRIPTION OF DRAWINGS

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be made to the following detailed description taken in connection with the accompanying drawings, in which.

DETAILED DESCRIPTION

Before the present methods, systems and assays are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cell and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Optional" or "optionally" means that the subsequently described event or circumstance may or may not occur, and that the description includes instances where the event occurs and instances where it does not.

"Administering" when used in conjunction with a therapeutic means to administer a therapeutic to a patient whereby the therapeutic positively impacts the tissue to which it is targeted. Thus, as used herein, the term "administering", when used in conjunction with cancer therapy, can include, but is not limited to, providing a treatment into or onto the target tissue; providing a treatment systemically to a patient by, e.g., intravenous injection whereby the therapeutic reaches the target tissue; providing a treatment in the form of silencing expression of a specific gene. "Administering" a composition may be accomplished orally, by injection, topical administration, or by these methods in combination with other known techniques.

The term "tissue" refers to any aggregation of similarly specialized cells which are united in the performance of a particular function.

The terms "antisense", "antisense oligonucleotides," "antisense oligomer," and "antisense compound" are used interchangeably and refer to a compound having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The antisense oligonucleotide includes a sequence of purine and pyrimidine heterocyclic bases, supported by a backbone, which are effective to hydrogen-bond to corresponding, contiguous bases in a target nucleic acid sequence. The backbone is composed of subunit backbone moieties supporting the purine and pyrimidine heterocyclic bases at positions that allow such hydrogen bonding. These backbone moieties are cyclic moieties of 5 to 7 atoms in length, linked together by phosphorous-containing linkages one to three atoms long. While antisense oligonucleotides are a preferred form of antisense compound, the present invention comprehends other oligomeric antisense compounds, including but not limited to oligonucleotide mimetics. Antisense compounds include ribozymes, external guide sequence (EGS) oligonucleotides (oligozymes), and other short catalytic RNAs (i.e., siRNA) or catalytic oligonucleotides which hybridize to the target nucleic acid and modulate its expression.

As used herein, the terms "gene" or "target gene" mean a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof.

The phrase "gene silencing" refers to a process by which the expression of a specific gene product is lessened or attenuated. Gene silencing can take place by a variety of pathways. Unless specified otherwise, as used herein, gene silencing refers to decreases in gene product expression that results from administering an inhibitor of gene expression. Inhibitors of gene expression include but are not limited to DNA, RNA, shRNA, siRNA, antibodies, small molecules, proteins, peptides, peptidomimetics, therapeutic agents, pharmaceutical compositions, drugs, and combinations of these agents.

As used herein, "inhibit" or "inhibition" means that the activity of a gene expression product or level of RNAs or equivalent RNAs encoding one or more gene products is reduced below that observed in the absence of the nucleic acid molecule of the invention.

As used herein the term "inhibitor" means any active agent that inhibits cell growth when administered to cells. Inhibitors include but are not limited to DNA, RNA, shRNA, siRNA, antibodies, small molecules, proteins, protein mimetics, peptides, peptidomimetics, therapeutic agents, pharmaceutical compositions, drugs, and combinations of these. The inhibition with an inhibitor preferably is below that level observed in the presence of an inactive or attenuated molecule that is unable to mediate an inhibition response. Inhibition of gene expression with the inhibitor of the present claimed invention is preferably greater in the presence of the inhibitor than in its absence.

As used herein, the term "therapeutic" means an agent utilized to treat, combat, ameliorate, prevent or improve an unwanted condition or disease of a patient. Embodiments of the present invention are directed to regulating cancer cell growth.

The term "siRNA" refers to small inhibitory RNA (also known as short interfering RNA or small interfering RNA) duplexes that induce the RNA interference (RNAi) pathway. The RNAi pathway is a partially characterized pathway whereby small inhibitory RNA (siRNA) act in concert with host proteins (e.g., the RNA induced silencing complex, RISC) to degrade messenger RNA (mRNA) in a sequence-dependent fashion. These molecules can vary in length (generally 18-30 basepairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region (shRNA). The siRNA can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides.

As used herein, the term "small interfering nucleic acid molecule", or siRNA, refers to any nucleic acid molecule that is capable of modulating the expression of a gene by RNA interference (RNAi), and thus encompasses short interfering RNA (siRNA), short interfering DNA (siDNA), double-stranded RNA (dsRNA), double-stranded DNA (dsDNA), complementary RNA/DNA hybrids, nucleic acid molecules containing modified (semi-synthetic) base/nucleoside or nucleotide analogues (which may or may not be further modified by conjugation to non-nucleic acid molecules, custom modified primary or precursor microRNA (miRNA), short hairpin RNA (shRNA) molecules, and longer (up to one kb or more), dsRNA or hairpin RNA molecules, so long as these do not activate non-specific interference, for example via interferon. The hairpin region may be short (e.g. 6 nucleotides), long (undefined length), or may include an intron that is efficiently spliced in the targeted cells or tissues. Additionally, multiple tandem repeats in one orientation (for example, three or more short sense repeats) are included under the definition of siRNA, as these can elicit a potent RNAi like response in some systems.

The term "transfection" refers to a process by which agents are introduced into a cell. The list of agents that can be transfected is large and includes, but is not limited to, siRNA, sense and/or anti-sense sequences, DNA encoding one or more genes and organized into an expression plasmid, proteins, protein fragments, and more. There are multiple methods for transfecting agents into a cell including, but not limited to, electroporation, calcium phosphate-based transfections, chemical transfection, cationic lipid transfection, DEAE-dextran-based transfections, laser mediated transfection, lipid-based transfections, molecular conjugate-based transfections (e.g., polylysine-DNA conjugates), microinjection, non-lipid based transfection, ostmotic lysis transfection, pinocytosis transfection, viral delivery systems and others.

The terms "mimetic," "peptide mimetic," "modified peptide," and, "peptidomimetic" are used interchangeably herein and generally refer to a peptide, partial peptide or non-peptide molecule that mimics the tertiary binding structure or activity of a selected native peptide or protein functional domain. A dimer of this compound is a molecule which mimics the tertiary structure or activity in two separate and distinct regions of the subject molecule. These peptide mimetics can include chemically modified amino acids or peptides, as well as non-peptide agents such as small molecule drug mimetics.

Currently, efficacy of potential chemotherapeutic agents must be tested in vivo. However, screening potential active agents for chemotherapeutic effects in this manner is time consuming and expensive, and testing for therapeutic effects on different cancer types can make development of cancer treatments prohibitively expensive. Therefore, a high-throughput, automated, and quantitative assay is beneficial.

The methods and devices of the present invention have been designed to use a chip containing active agents at high-density for testing anchorage-independent cell growth. Cells are plated on the chip or slide and allowed to grow in the presence of the active agents. Each cell on a specific spot will receive the active agent due to high transfection efficiency of the active agent. The concentration of active agent required for suppression of the tumorigenic phenotype can be similarly optimized. These method and device presented herein allow the efficient testing of even very small amounts of tumorigenic tissue, and rapid imaging and quantification of colony growth can be accomplished by labeling individual cells of the tumorigenic tissue, for example by fluorescently labeling each cell.

Figure 1:
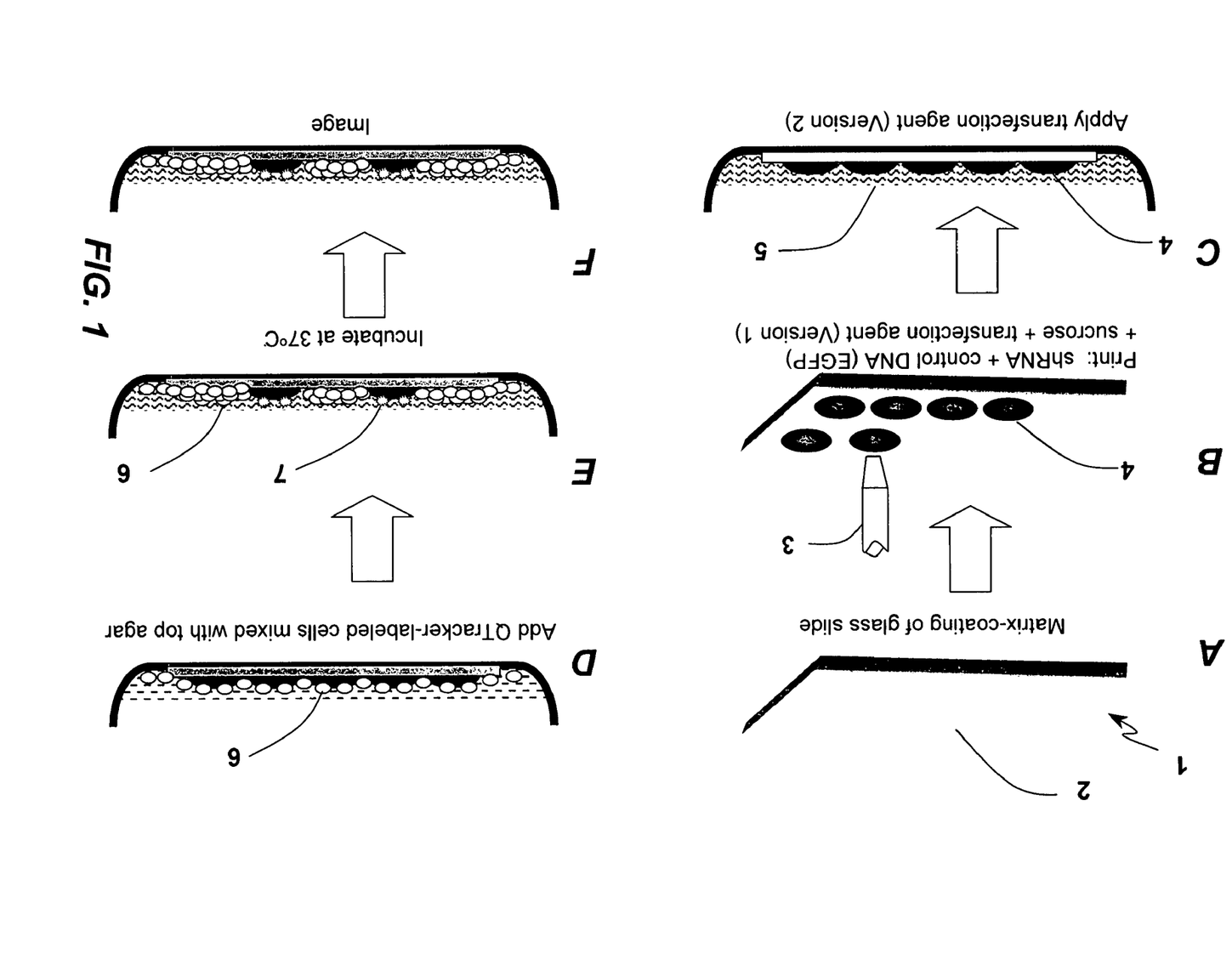
FIG. 1. Depicts one embodiment of a high-throughput, one-step transfection and anchorage-indepenedent assay device and method of the present invention.

In reference to FIG. 1, a slide 1 can be coated with a layer of matrix that allows anchorage-independent, three-dimensional cell growth 2. A spotter 3 can be used to imprint spots of active agents in or onto the slide 4. Transfection agent 5 can then be added to the matrix, and cells 5 can be plated onto the slide. The cells will take up the active agent, and spots that hold an active agent that inhibits cell growth will discourage colony formation and by in some cases killing the cells 6, while unaffected cells will continue to grow 5. After incubation the slide can be imaged to determine which active agents inhibit cell growth.

In one embodiment of the current invention, the cancer cells employed in the methods and devices are labeled. The label may be an optically detectable label. For example, labels may be selected from chemiluminescent labels, fluorescent labels, and enzymes that produce a visible color change.

The methods and devices of the present invention do not require staining of cells with toxic dyes, and therefore, allows for observation of cell growth or inhibition of cell growth in real time. While most anchorage-independent growth assays use tetrazolium salt, 3-(4,5-dimethylthiazol-2-yl)-2,5-diphenyltetrazolium bromide (MTT) to stain colonies, which kills the cells, recent studies have shown the usefulness of Quantum Dots™ (QD) for in vitro and in vivo imaging live cells. QDs are inorganic fluorescent semiconductor nanocrystals that are easily adaptable for live cell imaging. Unlike organic fluorophores, QDs are ideal for long-term imaging because they are photostable, resistant to enzymatic and chemical degradation in living cells, nontoxic, and can be passed through up to 6 generations of daughter cells. QDs have allowed live cell imaging of cultured cells, *Xenopus* embryos, zebrafish embryos, tumor cell xenografts in mice, and mouse blood vessels. Thus, the use of QDs as a fluorescent label allows for the observation of growth or inhibition of growth for more than 10 days, and the effect of an active agent on cell growth can be observed in real time. Other live cell labeling may be used, including, for example, EGFP, PlxBeads™ and the like.

In a particularly preferred embodiment of the present invention, QD's are used to label cell and tissues plated on the anchorage independent cell growth chip.

In one embodiment, a method for high-throughput testing of the effects of an active agent on anchorage-independent growth of cancer cells is provided. The method may include the use of microarray technology. Microarray technology may decrease the time required for such an assay by allowing administration of the active agent on the biochip, allowing for testing multiple active agents in parallel, decreasing the reagents required, and allowing live colony growth imaging.

In another embodiment, a device for screening agents comprises a biochip, wherein the biochip includes active agents, siRNA, DNA or shRNA-expression vectors, small molecules, antibodies, potential cancer drugs, small molecules, proteins, peptides, peptidomimetics or other prospective cancer treatments is provided. The active agents may be embedded at a high-density in a three-dimensional matrix that selectively allows tumor, but not normal cells, to grow or imprinted on top of the matrix. Labeled cells may be applied to the biochip in a matrix mixture that enables anchorage-independent growth, while blocking or decreasing cell migration. Individual cells may incorporate the underlying treatment and form fluorescently-labeled colonies. The absence or suppression of colony growth indicates that the underlying treatment blocks tumorigenic cell growth, since the cells can no longer grow in three-dimensions. Colony number and growth can be quantified using conventional fluorescent imaging systems and software. However, specialized software may be developed for data management, analysis, and user interface specifically with this system.

In one embodiment, nucleic acids may be incorporated into cells grown in soft agar. Previously, nucleic acids mixed with either gelatin or matrigel were used in reverse transfection reactions. Both substances promote growth of cultured cells by allowing cellular attachment to the surface of the reaction vessel which adds variable that might affect cellular response to active agents. To eliminate this variable and test cancer cell growth in a more physiological appropriate setting, anchorage-independent growth or three-dimensional growth on synthetic matrices is determined. Non-limiting, commercially available examples of these matrices include Polylactide-co-glycolide (PLGA), Alginate, and PuraMatrix™. These matrices promote three-dimensional cell growth without activating integrin cell signaling; however they also promote cell attachment. It should be appreciated that any such matrix that provides the above-mentioned properties and promotes three-dimensional growth of cancer cells without promoting cell-to-cell or cell-to-slide attachment, cell-to-cell signaling and integrin signaling may be used and are within the purview of those ordinarily skilled in the art. For example, the semi-solid matrix medium may comprise agar, agarose, methylcellulose, hydrogels, including, but not limited to, methylcellulose, hydrogels, alginate hydrogel (5% alginate+5% collagen type I), Chitosan, hydroactive hydrocolloid polymer gels, Polyvinyl alcohol-hydrogel (PVA-H), collagen vitrigel, PHEMA (poly(2-hydroxylmethacrylate)) hydrogels, PVP/PEO hydrogels, BD Puramatrix hydrogels, and copolymers of 2-methacryloyloxyethyl phophorylcholine (MPC). These matrices should also allow efficient spot size and density while retaining good scanner resolution.

High-density screening requires the use of minimal matrix material that can reliably provide sufficient colony growth. Standard soft agar protocols may be used to coat the slides. Matrix can be either applied as a coating or individually delivered to each spot/well. QD-labeled cells may be applied to matrix coated slides, and colony number per square micron may be assessed at time intervals in culture by automated or manual counting as previously described.

Minimal matrix thickness may be determined, where different volumes of base matrix are applied prior to culturing of QD-labeled cells on the biochip. Layer thickness is inversely proportional to spot/well diameter. In one embodiment, the thickness of the matrix is about 1 mm for a 3 mm diameter well or spot. In another embodiment, the base matrix thickness could be as small as 100 micron for an about 100 micron diameter well. Generally, the matrix is about 0.1 mm to about 1 mm in thickness can be designed to allow imaging of colonies in each spot or well on the slide.

Each type of matrix-coated slide can be tested for growth and imaging of different cell lines. For example, growth of transformed breast cancer cell lines (MCF-7 or MDA-MB-231) can be compared to immortalized NIH-3T3 fibroblast cells. MCF-7 and MDA-MB-231, but not NIH-3T3 cells should form colonies in soft agar. All three cell types will, however, grow on Alginate and Puramatrix™ coated slides. Generally, preferred matrices allow substantially no cell attachment or migration. However, the amount of cell migration should be limited to ensure that distinct colonies form on soft agar slides allowing growth of detectable colonies in spots.

In a particularly preferred embodiment of the current invention, the matrix selectively allows the growth of transformed cancer cells but not of normal cells. Therefore, the biochip is able to distinguish between normal cells and cancer cells.

In a further embodiment, glass slides may be prepared by applying a base agar layer to the slide, and then spotting these coated slides with a mixture of shRNA containing DNA expression vectors suspended in sucrose and transfection agent. The components may be manually deposited using a micropipette or similar device. Following slide preparation, QD-labeled breast cancer cells that have been mixed with top agar will be applied to slide. Slides containing cells will then be incubated for 2-7 days, and fluorescence signal can be obtained periodically throughout the incubation period to evaluate colony growth. Regions devoid of growth will indicate effectiveness of cancer inhibition by shRNA.

A mechanism for automatic deposition of reagents on the matrix-coated slides may be used. There are 3 broad approaches to disposition of spotted materials on microarray slides: contact, non-contact, and on-chip synthesis systems. Non-contact systems are best when a small number of samples must be spotted very frequently. Contact systems are used for printing thousands of small samples, and on-chip synthesis is not yet able to provide a sufficient amount of full-length oligonucleotide to support reverse transfection.

A spotter that is capable of providing nanometer scale accuracy is preferred, for example QTracker™. For optimal for spotting on three-dimensional surface chemistry, a spotter should provide controlled dwell time of pin tip on slide surface and control over the z-axis. A peltier plate chiller, HEPA filter, and humidity control provide environmental control and a high-pressure wash station and sterilizer clean the pins and eliminate carryover. This spotter can also be equipped with a UV light to sterilize all equipment prior to spotting for tissue culture purposes.

Test printing a Cy3-labeled oligonucleotide on matrix-coated slides will allow the visualization of the deposited nucleic acids, and several variables will be assessed: pin type, z axes settings, and chamber humidity. High density spotting on GAPSII slides (65,536-100,000 spots/slide, with 90-120 μm spot diameter) has been achieved using the 65 or 75 μm split pins, however, either solid or split pins may be used. For the purposes of this invention, from 1-150,000 spots may be present on a matrix coated slide.

Chamber humidity and z-axes settings will determine the success of high-density printing. The spots should retain their coating during the printing process. Chamber humidity is important for ensuring that the matrix does not become dry, and z-axis settings will allow control over how deep the pins will go into the matrix creating a small well delineating each spot. Spot size can be controlled by pin dwell time using split pins. Shorter dwell times may also limit distortion in matrix chemistry. In the event that matrix integrity becomes distorted during the printing process, non-contact printing approaches may be considered.

Spot sizes ranging from about 300 to about 500 μm in diameter with center-to-center distances ranging between about 300-1000 μm have been reported to have successfully been used for reverse transfection of cultured cells attached to GAPSII glass slides. The system uses cells grown embedded in the soft agar that should not migrate for the duration of the experiment. Thus, the spot-to-spot distance may be smaller. Therefore, the system has been designed to utilize smaller spot sizes and spot-to-spot distances allowing simultaneous testing of a large number of shRNAs.

A QArray™ spotter equipped with different size pins may be used to generate spots of Cy3-labeled oligonucleotide (green) ranging from about 65-350 μm in diameter and spot-to-spot distance of about 100-800 μm. QD-labeled MDA-MB-231 breast cancer cells may be cultured on slides. The number of colonies per spot will be determined after about 5-7 days of incubation and the Cy3-dye will determine overlap between the spots.

In one embodiment, spot sizes that allow the imaging and quantification of 30-50 colonies per spot and spot-to-spot distances that restrict overlap of Cy3-label DNA between spots may be used. Preliminary results suggest the minimum spot diameter may be between about 65-100 μm. 65 or 75 μm split pins can allow high-density spotting that will allow simultaneous testing of entire shRNA libraries or siRNA libraries on a single slide.

In another embodiment, a silicone rubber isolator similar to about 100 μm diameter and about 150 μm center-to-center distance culture wells may be used. The QArray™ spotter will be used to spot slides equipped with these silicone isolators, and the depth of the wells will not be an issue since the z-axis control on the arrayer allows spotting into deeper wells found in 96-well plates. This isolator will create a seal on glass slides and will prohibit diffusion of material between spots.

Spots may be optionally separated from one another using wells created within the slide, wells created by placing a removable member on the slide wherein the removable member contains a plurality of holes that act to separate spots placed within a hole from the spots surrounding the hole, or a plurality of demarcations etched into the slide that act to separate one spot from the spots surrounding that spot. Anyone skilled in the art could create these wells by a number of methods, including photolithography, injection molding, stamping, printing, compression molding, micromachining, laser cutting, or any such techniques that can produce micron scale feature on a solid substrate.

In one embodiment of the current invention, a calibration chip is used to optimize the cancer cell culture modalitites, specificity of active agents, transfection method, and reproducibility of the assay prior to high density studies. The calibration chip will contain all necessary positive and negative controls and will allow the determination of culture and transfection conditions for any cell type.

In one embodiment of the current claimed invention, RNAi is used to inhibit the expression of individual human genes. Each spot on the chip is seeded with a different RNA molecule that selectively silences a single specific target gene.

Spots where cancer cell growth is inhibited implicate the expression of the gene corresponding to the RNA molecule in the cancerous phenotype.

RNA interference (RNAi) has become the technology of choice for inhibiting gene expression in eukaryotic cells and plants. RNAi methodology targets specific sequences in the inhibited gene making it a powerful tool for functional genomics and drug discovery. Inhibition occurs when double stranded RNA (dsRNA) that is homologous to the gene of interest is introduced into a cell. dsRNA is recognized and cleaved by a dsRNA specific endonuclease, Dicer, producing small interfering RNA (siRNA). siRNA consist of small segments of dsRNA (no longer than 30 base pairs) with 2 nucleotide 3' overhangs. These segments are recognized and bound by PIWI-family member proteins to form an RNA-Induced Silencing Complex (RISC). The sense strand of the siRNA is integrated into RISC and RISC uses this sequence to recognize and cleave mRNA site-specifically at this sequence. mRNA that has been cleaved by RISC no longer contain capping molecules, is recognized by cellular machinery as aberrant, and degraded, which suppresses or silences the expression of the target gene.

The design of siRNA is critical to its effectiveness, and several software packages have been developed for the efficient design of siRNA. siRNA should be complimentary to a target sequence on mRNA that is within a translated region of the gene and not close to 3' or 5' untranslated regions or within untranslated (intron) sequences, although gene silencing was observed in some instances when these sequences were targeted. The nucleotide composition, G/C content, and location of adenosine dimers is essential for successful RNA silencing. It is recommended to have A/U at 5'-end of antisense strand, G/C at 5'-end of sense strand, AU-rich 5'-terminal third of antisense strand, and no GC stretches over 9 base pairs long. Following these criteria, RNAi inhibitors can be designed for any human gene based on the human genome sequence.

Short hairpin RNA (shRNA) may also be utilized to obtain gene specific RNAi silencing. shRNA can be expressed within a target cell from a DNA construct that contains a gene whose product is RNA that forms tight hairpin structures. Since the hairpin structures create short dsRNA-like RNA molecules, they are recognized and cleaved into siRNA by Dicer. RISC complexes are then formed using these siRNA, and targeted mRNA are degraded by the pathway illustrated above. siRNA is not very stable, however shRNA can be expressed from standard expression vectors as well as retroviral or lentiviral expression systems and expression of shRNA can be maintained for extended periods. shRNA and siRNA libraries targeting a large number of human genes are now commercially available. The invention disclosed herein will allow these libraries to be screened for cancer therapeutics.

In the examples described herein, shRNA was used as the active agent, however the devices and systems of the present invention can be used to test the efficacy of other compounds, molecules or agents, including but not limited to, therapeutic agents, pharmaceuticals, antibodies, drugs, expression vectors that contain genes that suppress tumor gene function, proteins, peptides, peptidomimetics, or other active agents.

The systems and devices described herein may be used to identify siRNAs capable of inhibiting expression of any gene responsible for cancer cell growth. Recently generated shRNA libraries have been developed that targeted thousands of human genes. For example, the Nki library uses 23,742 vectors to target 7,914 human genes with 3 shRNAs for each gene, and six p53 pathway genes involved in growth of transformed cells have been identified using this library by testing the ability of shRNAs to stimulate colony growth in soft agar. Future libraries are anticipated that will provide complete coverage of all human genes which will allow the identification of previously unknown cancer genes. In one embodiment of the present invention, an shRNA library that encompasses the entire human genome may be used in the system. In another embodiment, a shRNA library of portions of the genome may be used.

In one embodiment of the current claimed invention, a single biochip or set of biochips contain individual spots containing inhibitors for every gene in the human genome.

In another embodiment, a single biochip or a set of biochips contain individual spots containing inhibitors for every gene expressed from the human genome.

In another embodiment of the current invention, a single biochip or set of biochips contain individual spots for every gene or every expressed gene of a mammal or other organism.

In one embodiment, a method of screening for siRNA that affects or inhibits cancer cell growth is provided. The method comprises applying a semi-solid medium to a solid surface, adding siRNA and a transfection agent in demarcated spots, applying cancer cells to the solid surface, incubating and measuring cancer cell growth in real-time.

In another embodiment, a high-throughput assay for screening a plurality of siRNA for inhibition of cancer cell growth is provided. The assay comprises providing a siRNA embedded at a high density in a semi-solid medium, providing cancer cells and measuring growth of the cancer cells.

In a further embodiment, a device for screening a plurality of siRNA for inhibition of cancer cell growth is provided. The device comprises siRNA vectors, a semi-solid media or three-dimensional matrix, and cancer cells. In a further embodiment, the siRNA vectors may be embedded into the media or matrix and further embedded at a high density.

Highly efficient delivery of shRNA into cancer cells growing on the system is beneficial. Several transfection agents are now commercially available, and both lipid-based transfection agents such as X-treme GENE™ (Roche Applied Science), siIMPORTER™ (Upstate), Lipofectamine 2000™ (Invitrogen), RNAiFect™ and Effectene™ (QIAGEN), as well as non-lipid-based agents, such as GeneEraser™ (Stratagene), RiboJuice™ (Novagen), EXPRESS-si™ (Genospectra, Inc.), and Arrest-In™ (Open Biosystems) were tested for transfection efficiency. Any of these reagents can by used in the system. In one embodiment, a cationic polymer that protects DNA in the cytoplasm and promotes entry into the nucleus (i.e., Arrest-In™) may be used. Preliminary studies indicate that this transfection agent provides at least equivalent transfection efficiency than other transfection agents in both adherent cells and cells grown in suspension. Other methods may be employed, including but not limited to, chemical transfection, laser-mediated transfection, micro-injection, pinocytosis mediated transfection or electroporation.

In one embodiment of the present invention, transfection occurs in a single step. That is, transfection occurs on the biochip itself and not as a separate step preceding plating of the cells.

Transfection efficiency may also depend on method of delivery of the transfection agent. Therefore, separate tests will be completed in which transfection agent is added concurrently with spotting and after spotting but prior to the addition of cells will be tested separately, and the number of the colonies on each chip capable of expressing EGFP from a transfected EGFP expression vector will be monitored. QD-labeled cells will be used in this assay to identify all live cells. After incubation for 3-7 days, EGFP and QD labeled colonies will be counted to determine transfection efficiency. All live cells are expected to form fluorescently-labeled red colonies, while transfected colonies will also be green as a result of EGFP expression. Transfection efficiency will be measured by counting number of green colonies and dividing by the total number of colonies in each spot. We anticipate optimizing all the above-mentioned variables in several different cell lines to determine maximum, universal transfection efficiency.

Although chemical transfection is efficient, in another embodiment of the instant invention, lentiviral delivery systems may be used to transfect tested cells. Lentiviral delivery systems are known to provide very efficient transfection, and lentiviral-based shRNA libraries are commercially available.

The nucleic acid to transfection agent ratio may be a determinant of transfection efficiency. Thus, three different concentrations of DNA will be tested in combination with three different concentrations of transfection agent. Starting doses will be calculated by proportionately scaling down manufacturer's recommended dosage. Controls will include (a) no treatment, (b) transfection agent without DNA, and (c) transfection agent combined with an expression vector lacking EGFP, and the optimal transfection agent to DNA ratio will be determined.

Silencing efficiency of shRNA may be determined by testing the ability of shRNA to suppress expression of a co-transfected reporter gene. Spots will be generated containing one of the following mixes with different concentrations of nucleic acids: 1) EGFP expression vector, 2) EGFP expression vector mixed with pooled shRNA vectors against EGFP, and 3) EGFP expression vector mixed with non-specific scrambled shRNA or shRNA targeting firefly luciferase, a gene absent in mammalian cells to show specificity in gene silencing.

Clusters of EGFP producing (green) and QD containing (red) cells are expected to be observed everywhere on the slide except in spots where shRNA for EGFP is present. In these spots, only red colonies should be present since EGFP expression has been silenced. shRNA dosage response, and temporal pattern of gene silencing will be optimized using this assay. Since shRNA vectors are stable, gene silencing should be observed throughout the duration of incubation (1-3 weeks or more). Understanding the silencing efficiency of EGFP shRNA in soft agar will help to identify the optimal shRNA concentration necessary for suppression of genes with varying levels of expression.

Once the shRNA concentration necessary to suppress gene expression has been determined, the ability of shRNA incorporated from the assay to suppress the expression of cancer genes will be tested by inhibiting of estrogen receptor α (ERα) in breast cancer cells and suppressing oncogene expression in an inducible murine fibroblast cancer cell line.

One embodiment of a high-throughput assay and device of the present invention is depicted in FIG. 1. The device may comprise matrix-coated solid surfaces, for example glass slides, are printed with a mixture of shRNA/DNA suspended in sucrose (using QArray™, Genetix, Inc.). A transfection agent may be added by methods known to those of ordinary skill in the art, such as, for example by mixing transfection agent (e.g., Effectene™, Arrest-In™) with the spotting solution (Version 1) or coating after spotting and prior to addition of cells (Version 2.) Cells, pre-incubated in QTracker™ 655 solution and mixed with agar at 37° C., may be applied to the solid surface. The cells may be incubated, for example for 2-7 days at 37° C. with 5% CO2. The fluorescence signal may be obtained periodically through the incubation period to evaluate colony growth. Regions devoid of growth will indicate effectiveness of cancer inhibition by shRNA.

Although the present invention has been described in considerable detail with reference to certain preferred embodiments thereof, other versions are possible. Therefore the spirit and scope of the appended claims should not be limited to the description and the preferred versions contained within this specification. This invention and embodiments illustrating the method and materials used may be further understood by reference to the following non-limiting examples.

EXAMPLE 1

This example illustrates a device for high-throughput screening. The device uses Culture Well chambered coverslips (Grace Bio-labs, Inc., Bend, Oreg.), with each spot being 3 mm in diameter. All components were manually deposited using a micropipette. After application of a base agar layer (0.8%), shRNA pre-mixed with Arrest-In™ (Open Biosystems Inc., Huntsville, Ala.) was applied, followed by QTracker™ (Quantum Dot Corporation, Hayward, Calif.)-labeled breast cancer cells (MDA-MB-231) mixed with top agar (0.4%). Cells were incubated in a CO2 incubator at 37° C. and monitored using an inverted fluorescence microscope 1, 4, 5, and 7 days later.

EXAMPLE 2

Using the device of Example 1, anchorage-independent growth of MDA-MB-231 breast cancer cells stably transfected with an Enhanced Green Fluorescence Protein (EGFP) expression vector for live cell visualization and imaging was obtained. While cells growing on uncoated tissue culture surfaces (FIG. 1A) attached to the surface and developed processes for cell-cell contact and migration, cells growing on the assay formed localized colonies that were embedded in the agar (FIG. 1B). All EGFP-labeled colonies (FIG. 1B) also stained for QTracker™ (FIG. 1C, red), with the red signal being stronger and more photostable. A shorter camera exposure time was required for capturing comparable signals for QTracke™ and EGFP (1 second for QTracker™ as opposed to 10 seconds for EGFP). Background fluorescence was very minimal with QTracker™ and becomes only evident with longer exposure times. Colonies could be imaged at multiple intervals after culturing with no fading of the QTracker™ signal. We have been able to examine colony growth 1, 4, 5, and 7 days after plating. Shown are images of colonies taken after 5 days in culture. As seen in FIG. 1C, many cell divisions have already occurred after 5 days in culture and the QTracker™ signal remained stronger than EGFP.

Figure 2:
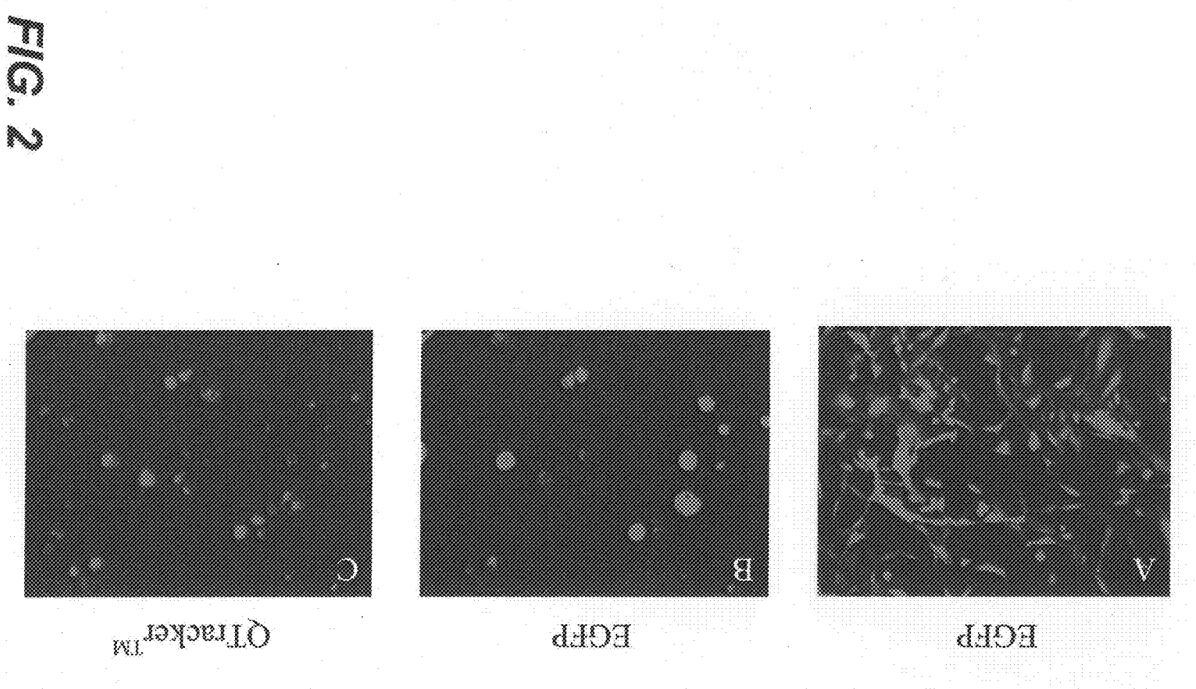
FIG. 2. Imaging of breast cancer cells expressing Enhanced Green Fluorescence Protein (EGFP) and labeled with QTracker™. A) Cells growing on conventional tissue culture surfaces (A, green) attach and spread out their processes, while cells growing on the device remain localized and form colonies that are EGFP (B, green) and QTracker™ (C, Red)-labeled. Magnification: 200×.

To determine whether the QTracker™ signal can faithfully reflect colony number, number of colonies obtained by manual counting and QTracker™ signal as determined by measuring "percent thresholded area" using the Metamorph™ software (Molecular Devices Corporation, Sunnyvale, Calif.). Analysis of the QTracker™ signal required first identification of the colonies under phase contrast and fluorescence, followed by thresholding of the area occupied by colonies, and determination of the percent threshold area were compared. The thresholded area is the area occupied by colonies. The percent thresholded area is the percentage of the total area of interest that has been thresholded. A linear regression analysis was performed to determine whether the percent thresholded area could be used as a reflection of QTracker™ signal. The Pearson Correlation Coefficient (r) was 0.79. Testing the null hypothesis (H (null):r=0) to determine significance of this relationship, gave us a t statistic=6.84 with df=29, and a P-value <0.0001. As shown in FIG. 2, a significant correlation between QTracker™ signal as determined by percent thresholded area and colony number can be determined.

These observations demonstrate the ability to perform high-throughput anchorage independent growth assays. Colony growth over time may be visualized and quantified. The assay circumvented the problem of cell migration observed in other high-throughput reverse transfection assays, where cell attachment and migration is problematic for maintaining boundaries between individual spots. In addition, the use of QDs to visualize colonies allows for live colony visualization and quantitative analysis of colony growth over time.

EXAMPLE 3

Figure 3:
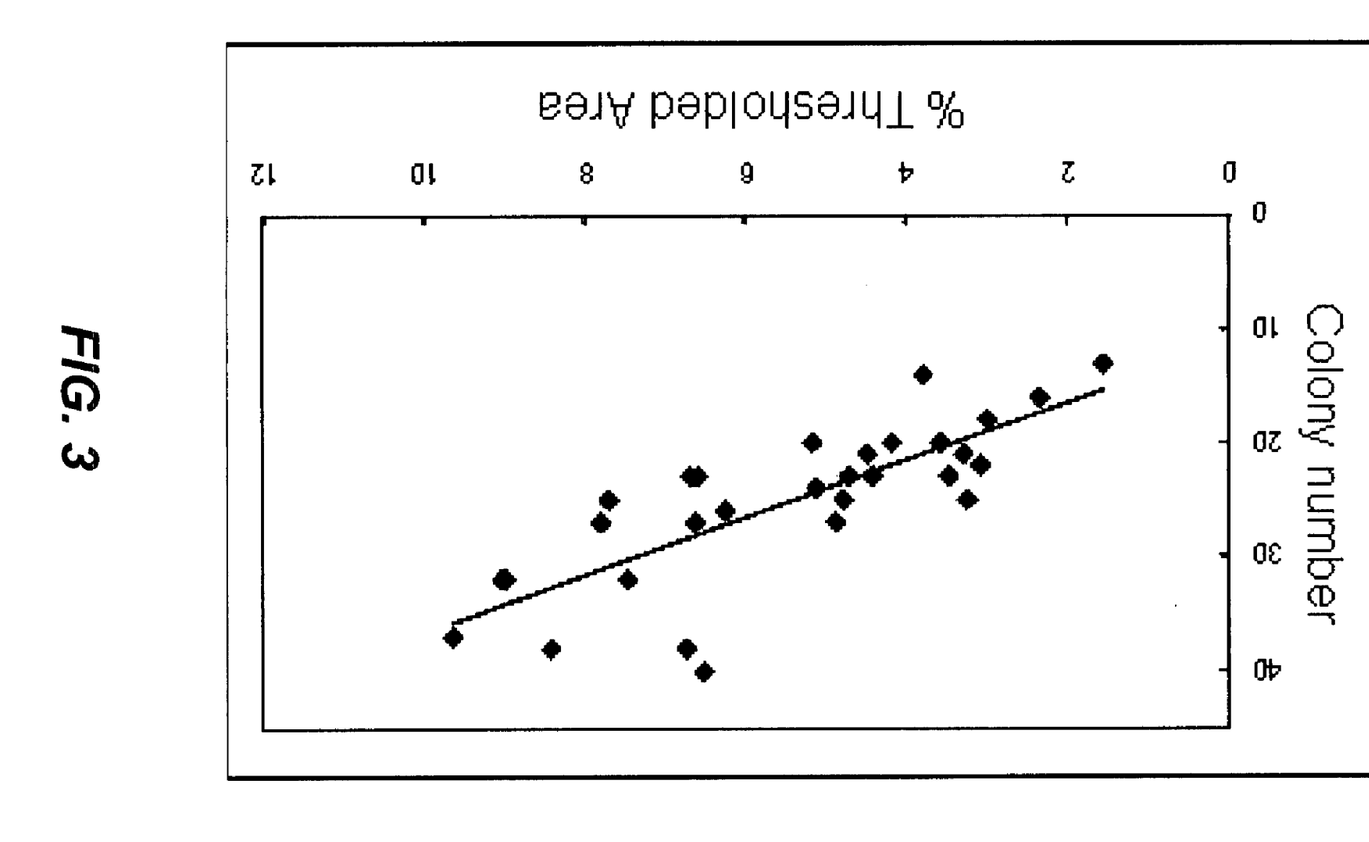
FIG. 3. Scattergram showing correlation between QTracker™ signal, expressed as percent (%) thresholded area, and colony number.

In this example, the suppression of gene expression using siRNA by testing silencing of EGFP in cells engineered to express EGFP was performed. Arrest-In™, a polymeric transfection agent that protects DNA in the cytoplasm and promotes entry into the nucleus of transfected cells, was tested for the ability to catalyze reverse transfection of MDA-MB-231 breast cancer cells stably expressing EGFP with EGFP shRNA. Different concentrations of Arrest-In™ (0.02, 0.05, and 0.1 µg) combined with anti-EGFP shRNA vector (0.01, 0.02, and 0.03 µg/spot) were tested. Results are depicted in FIG. 3, which shows side-by-side QTracker™ (A, red) and EGFP (B, green) images from cells transfected with 0.1 µg Arrest-In™ and 0.03 µg EGFP shRNA. Unlike control cells that received Arrest-In™ only (FIG. 1B, C), EGFP signal (FIG. 3B) was suppressed in some, but not all colonies exposed to EGFP shRNA. These tests suggest the feasibility of shRNA transfection and silencing of gene expression in breast cancer cells grown on a device of the present invention and suggest that reverse transfection can occur efficiently in cancer cells transfected with 0.1 µg Arrest-In™ and 0.03 µg EGFP shRNA.

EXAMPLE 4

Figure 4:
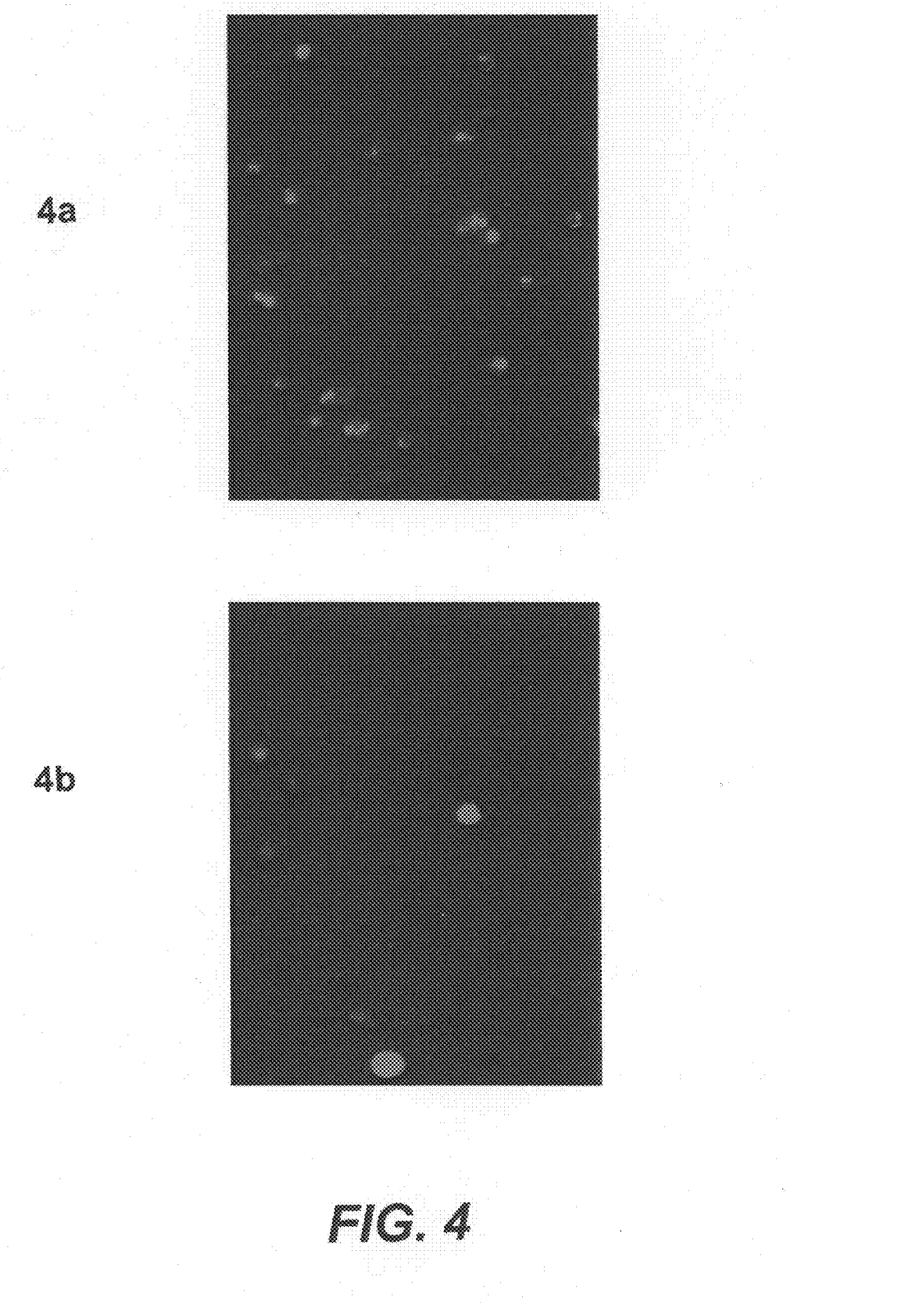
FIG. 4. Silencing of EGFP gene expression by EGFP shRNA. MDA-MB-231 cells expressing EGFP were labeled with QTracker™ and grown in spots containing Expression Arrest™ EGFP shRNA vector (0.03 µg) mixed with Arrest-In™ (0.1 µg). Colonies were examined 5 days after culture and imaged for QTracker™ (red—left) and EGFP (green—right). Magnification: 200×.
Figure 5:
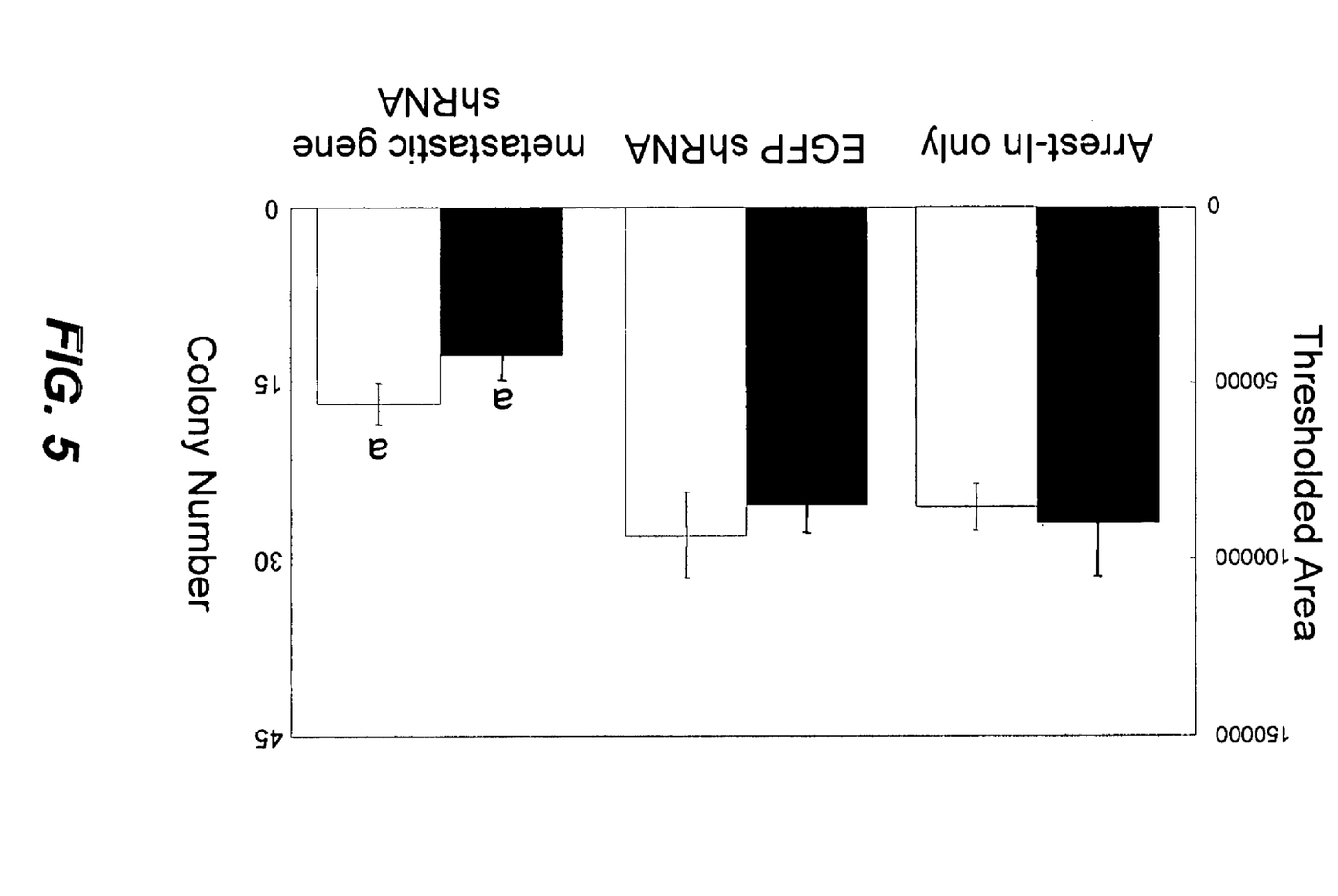
FIG. 5. Silencing of gene involved in breast cancer metastasis suppresses MDA-MB-231 colony growth on the device. After 7 days in culture, QTracker™ signal (Thresholded Area, black bars) and colony number (white bars) were measured. Each treatment was performed in 5 replicates. a $P<0.05$, Student's t-test.

The device of Example 1 was used to test the effect of metastatic gene shRNA (name of gene to be involved in cancer cell metastasis withheld) on MDA-MB-231 breast cancer cells. All cells were labeled with QTracker™ prior to application one the device. Controls included no Arrest-In™ and no shRNA, Arrest-In only with no shRNA, Arrest-In™ (0.1 µg) with vector lacking shRNA sequence, and Arrest-In™ with EGFP shRNA. Colonies were counted manually and the QTracker™ signal was determined in terms of thresholded area using the Metamorph Image Analysis Software™. As shown in FIG. 4, EGFP shRNA did not effect colony growth. For cells treated with EGFP shRNA, QTracker™ signal (ThresholdedArea) and colony number were comparable to no shRNA (Arrest-In™ only). Both colony number and QTracker™ signal were markedly suppressed after treatment with shRNA for the breast cancer metastasis gene. Cells transfected with vector lacking the shRNA sequence did not demonstrate any growth suppression. These observations demonstrate the ability of the device to identify shRNAs for genes involved in cancer cell growth.

EXAMPLE 5

The ability of ERα shRNA to suppress MCF-7 will be tested by administering different doses of ERα shRNA and control shRNA via a high-throughput, anchorage-independent device and monitoring colony growth of QD-labeled MCF-7 cells for 7 days. Controls will include unlabeled cells, labeled cells that receive no transfection agent, and labeled cells that receive no shRNA. The ability of shRNA to suppress ERcα expression killing MCF-7 cells plated on device will then be compared to the effects of the specific ERα antagonist, ICI 182,780. In these experiments, the dose of ICI 182,780 spotted on top of the base agar prior to administration of labeled MCF-7 cells will also be varied. Colonies will be manually counted under phase-contrast microscopy and automatically counted using a fluorescence microscopy and imaging software to measure QD signal. Dose response curves for ERα shRNA and ICI 182,780 will then be generated and compared. Dose-dependent suppression of colony formation in spots containing ICI 182,780 or ERα shRNA should be observed, while colony growth will be uninhibited in spots containing control RNA.

The murine fibroblast cancer cell line (NIH-3T3) is an inducible cancer model system meaning that these cells become transformed upon expression of a variety of oncogenes. The receptor tyrosine kinase Her-2/neu is the basis for the breast cancer drug Herceptin and is associated with poor prognosis in breast cancer patients. Over-expression of human Her-2/neu gene in NIH-3T3 cells results in a cancer-like phenotype, including the ability of these cells to grow in soft agar and form tumors in nude mice. Switching off Her-2/neu gene expression blocks growth of these tumor cells both in mice and in cell culture. Therefore, a cell line in which Her-2/neu expression can be suppressed using shRNA will be tested with a device of the present invention.

NIH-3T3 cells will be transformed with an Her-2/neu expression vector (NIH-3T3-Her2/neu), and various concentrations shRNA targeting this gene will be spotted on the device along with appropriate controls. Her2/neu expression from NIH-3T3-Her2/neu should be suppressed in cells contacted by anti-Her2/neu shRNA blocking colony formation. Cells contacted by control shRNA or no shRNA should continue to grow forming colonies. As in MCF-7 experiments, Herceptin studies will be completed in parallel. The number of colonies will be counted, dosage-dependent growth curves will be generated, and effects of anti-Her2/neu shRNA with Herceptin will be compared.

Imaging will be initially accomplished using a position-controlled inverted fluorescence microscope stage to enable automated precise localization of each spot incrementally in conjunction with image capture using a CCD camera. Once images are captured, image analysis software will define the area of interest, subtract background, threshold the image to identify labeled colonies as objects, create a region around these objects, and measure the percent thresholded area. Average colony size will also be determined. In one embodiment of the invention, these analyses can be carried out with existing computer programs, and in another preferred embodiment, software macros will be developed to automate these steps.

Accurate and specific quantification of colony number requires that image analysis is performed within the linear range of signal detection. Thus, the concentration of QD-labeled cells allowed to grow on a device of the present invention will be varied to determine the linear range, and experiments will be designed QD-labeled cell concentrations within this range. Manual colony counting will then be compared to automated data analysis. In these analyses, the image analysis software and manually counted results will be plotted relative to one another.

Our preliminary results suggest that we will be able to automate image acquisition and data analysis. Regular fluorescence microscopy worked well for imaging live colonies on this device. However, laser scanning confocal microscopy may be required for analysis of the high-density chip. In a preferred embodiment of the invention, a high-resolution laser confocal scanner that can detect signals from QDs, fluorophores, and EGFP and can scan at 5 micron resolution with a depth of focus ranging +/−1 mm will be used to analyze high-density devices.

A high-resolution laser confocal scanner has not been previously used for live cell imaging, so the effects of laser confocal scanning on colony growth will be tested by growing colonies on the device and scanning this biochip at different time intervals (1-10 days in culture). Controls will include parallel slides that are either not imaged until day 10 or imaged at the same time intervals using a regular fluorescence microscope. Colony number will then be measured as described above. In addition, the linear range for signal detection will be determined by imaging colonies obtained from different starting concentrations of cells. Again, the colony number obtained using the automated system will be compared with the number obtained manually to ensure accuracy of the analysis.

I claim:

1. A kit for assaying cells comprising:
   at least one slide comprising an upper surface;
   a base layer laid on said upper surface, said base layer comprising a first matrix and a plurality of spots, wherein the plurality of spots comprise a plurality of active agents; and
   a second matrix for mixing with, or for layering atop of, cells to be assayed, and for forming a top layer on top of the base layer;
   wherein the first matrix supports anchorage-independent cell groth when the kit is used; and wherein the second matrix limets cell migration and allows three-dimensional cell growth.

2. The kit of claim 1, wherein the first matrix and the second matrix are selected from soft agar, agarose, hydrogels, methylcellulose alginate hydrogel, polyvinyl alcohol-hydrogel, collagen vitrigel, poly(2-hydroxylmethacrylate) hydrogels, PVP/PEO hydrogels, copolymers of 2-methacryloyloxyethyl phophorylcholine and combinations thereof.

3. The kit of claim 1, wherein the first matrix and the second matrix comprise soft agar.

4. The kit of claim 1, wherein the plurality of active agents are selected from DNA, RNA, siRNA, shRNA, antibodies, small molecules, proteins, peptides, peptidomimetics, pharmaceutical compositions, drugs and combinations thereof.

5. The kit of claim 1, wherein the slide is selected from the group consisting of glass slides, plastic slides, polystyrene slides, quartz wafers, chambered coverslips and combinations thereof.

6. The kit of claim 1, wherein the kit further comprises cells to be assayed.

7. The kit of claim 6, wherein the cells are selected from the group consisting of cultured cells, cancer cells, tissue sample cells, tumor cells, tumor cells derived from the biopsy of a cancer patient, normal cells derived from a healthy patient, known cell lines, and combinations thereof.

8. The kit of claim 6, wherein the cells further comprise a detectable label.

9. The kit of claim 8, wherein the detectable label is selected from the group consisting of selectable markers, fluorescent markers, fluorescent nanocrystals, quantum dots, fluorescent proteins, bacterial enzymes, and combinations thereof.

10. The kit of claim 6, further comprising a means for observing the cells.

11. The kit of claim 10, wherein the means for observing cells is selected from microscopy, scanning, laser scanning, fluorescence detection, automated fluorescence detection, a CCD camera, cell counter, automated colony counter, the human eye, FACS and combinations thereof.

12. The kit of claim 1, wherein the plurality of spots comprise from about 1 to about 150,000 spots.

13. The kit of claim 1, wherein the diameter of each spot is from about 65 to about 120 μm.

14. The kit of claim 1, wherein the plurality of spots comprise siRNA.

15. The kit of claim 1, wherein spots are separated from one another by
   (a) using wells within the slide;
   (b) using wells created by placing a removable member on the slide, wherein the removable member contains a plurality of orifices that act to separate spots placed within an orifice from other spots; or
   (c) plurality of demarcations etched into the slide that acts to separate one spot from other spots.

16. The kit of claim 1, wherein the spots are separated from each other by using wells created by placing a removable member on the slide, wherein the removable member contains a plurality of orifices that act to separate spots placed within an orifice from other spots.

17. The kit of claim 1, wherein at least one of the plurality of active agents targets at least one gene.

18. The kit of claim 1, wherein at least one of the plurality of active agents targets at least one expressed gene.

19. The kit of claim 1, wherein the base layer further comprises at least one transfection agent selected from the group consisting of chemical transfection agents, lipid based transfection agents, cationic lipid transfection agents, non-lipid based transfection agents, electroporation, molecular-based transfections, laser mediated transfection, pinocytosis transfection, ostmotic lysis transfection, microinjection, viral delivery systems and combinations thereof.

20. The kit of claim 1, wherein the slide is a calibration chip comprising control agents.

21. The kit of claim 1, wherein the base layer and/or the top layer of matrix further comprises at least one transfection agent selected from the group consisting of chemical transfection agents, lipid based transfection agents, cationic lipid transfection agents, non-lipid based transfection agents, electroporation, molecular-based transfections, laser mediated transfection, pinocytosis transfection, ostmotic lysis transfection, microinjection, viral delivery systems and combinations thereof.

22. The kit of claim 1, wherein the base layer coats the upper surface of the slide.

23. The kit of claim 1, wherein the base layer is spotted on the slide.

24. The kit of claim 1, further comprising a plurality of wells.

25. A kit for assaying cells comprising:
   at least one slide comprising at least one well;
   a base layer laid within said well, said base layer comprising a first matrix and at least one spot, wherein the spot comprises an active agent, and
   a second matrix for mixing with, or for layering atop of, cells to be assayed, and for forming a top layer on top of the base layer;

wherein the first matrix supports anchorage-independent cell growth when the kit is used; and the second matrix limits cell migration and allows three-dimensional cell growth.

26. The kit of claim 25, wherein the first matrix and the second matrix are selected from soft agar, agarose, hydrogels, methylcellulose alginate hydrogel, polyvinyl alcohol-hydrogel, collagen vitrigel, poly(2-hydroxylmethacrylate) hydrogels, PVP/PEO hydrogels, copolymers of 2-methacryloyloxyethyl phophorylcholine and combinations thereof.

27. The kit of claim 25, wherein the first matrix and the second matrix comprise soft agar.

28. The kit of claim 25, wherein the active agent is selected from DNA, RNA, siRNA, shRNA, antibodies, small molecules, proteins, peptides, peptidomimetics, pharmaceutical compositions, drugs and combinations thereof.

29. The kit of claim 25, wherein the spot comprises siRNA.

30. The kit of claim 25, wherein the active agent targets at least one gene.

31. The kit of claim 25, wherein the active agent targets at least one expressed gene.

32. The kit of claim 25, wherein the base layer further comprises at least one transfection agent selected from the group consisting of chemical transfection agents, lipid based transfection agents, cationic lipid transfection agents, non-lipid based transfection agents, electroporation, molecular-based transfections, laser mediated transfection, pinocytosis transfection, ostmotic lysis transfection, microinjection, viral delivery systems and combinations thereof.

33. The kit of claim 25, wherein the kit further comprises cells to be assayed.

34. The kit of claim 33, wherein the cells are selected from the group consisting of cultured cells, cancer cells, tissue sample cells, tumor cells, tumor cells derived from the biopsy of a cancer patient, normal cells derived from a healthy patient, known cell lines, and combinations thereof.

35. The kit of claim 33, wherein the cells further comprise a detectable label.

36. The kit of claim 35, wherein the detectable label is selected from the group consisting of selectable markers, fluorescent markers, fluorescent nanocrystals, quantum dots, fluorescent proteins, bacterial enzymes, and combinations thereof.

37. The kit of claim 33, further comprising a means for observing the cells.

38. The kit of claim 37, wherein the means for observing cells is selected from microscopy, scanning, laser scanning, fluorescence detection, automated fluorescence detection, a CCD camera, cell counter, automated colony counter, the human eye, FACS and combinations thereof.

* * * * *

UNITED STATES PATENT AND TRADEMARK OFFICE
CERTIFICATE OF CORRECTION

PATENT NO.       : 7,537,913 B2
APPLICATION NO.  : 11/337215
DATED            : May 26, 2009
INVENTOR(S)      : Rula Abbud-Antaki

Page 1 of 1

It is certified that error appears in the above-identified patent and that said Letters Patent is hereby corrected as shown below:

Claim 1, Column 17, line 34, the term "groth" should read --growth--.
Claim 1, Column 17, line 35, the term "limets" should read --limits--.

Signed and Sealed this

Fourteenth Day of July, 2009

JOHN DOLL
*Acting Director of the United States Patent and Trademark Office*